(12) United States Patent
De Leon-Rodriguez

(10) Patent No.: US 8,679,453 B2
(45) Date of Patent: Mar. 25, 2014

(54) CONTRAST AGENTS

(75) Inventor: Luis M. De Leon-Rodriguez, Guanajuato (MX)

(73) Assignee: Universidad de Guanajuato, Guanajuato (MX)

( * ) Notice: Subject to any disclaimer, the term of this patent is extended or adjusted under 35 U.S.C. 154(b) by 744 days.

(21) Appl. No.: 12/748,445

(22) Filed: Mar. 28, 2010

(65) Prior Publication Data

US 2011/0009605 A1  Jan. 13, 2011

Related U.S. Application Data

(60) Provisional application No. 61/225,187, filed on Jul. 13, 2009.

(51) Int. Cl.
| | |
|---|---|
| *A61K 51/00* | (2006.01) |
| *A61M 36/14* | (2006.01) |
| *A61K 49/00* | (2006.01) |
| *A61K 31/00* | (2006.01) |
| *A61K 49/06* | (2006.01) |

(52) U.S. Cl.
CPC ........................................ *A61K 51/00* (2013.01)
USPC .......................................... 424/1.11; 424/1.65

(58) Field of Classification Search
None
See application file for complete search history.

(56) References Cited

U.S. PATENT DOCUMENTS

| | | | | |
|---|---|---|---|---|
| 4,880,008 A | * | 11/1989 | Lauffer | 424/9.363 |
| 5,403,572 A | * | 4/1995 | Gries et al. | 424/9.363 |
| 5,595,725 A | * | 1/1997 | Gries et al. | 424/9.34 |
| 7,279,150 B2 | * | 10/2007 | Lanza et al. | 424/9.361 |

FOREIGN PATENT DOCUMENTS

| | | | | |
|---|---|---|---|---|
| WO | WO0024429 | * | 5/2000 | A61K 49/00 |

OTHER PUBLICATIONS

Hanaoka et al. (J. Chem. Soc., Perkin Trans. 2001, 2, 1840-1843).*
Wieghardt et al. (Inorg. Chem. 1986, 25, 4877-4883).*
Corot et al. (J. Mag. Reson. Imaging 1998, 8, 695-702).*
Magerstädt et al. (Mag. Reson. Med. 1986, 3, 808-812).*
De Leon et al. J. Am. Chem. Soc. 2009, 131, 11387-11391.
Hanaoka et al: "Design and Synthesis of a Novel Magnetic Resonance Imaging Contrast Agent for Selective Sensing of Zinc Ion"; Chem. & Biol.; vol. 9; pp. 1027-1032 (Sep. 2002).

* cited by examiner

*Primary Examiner* — Michael G Hartley
*Assistant Examiner* — Melissa Perreira
(74) *Attorney, Agent, or Firm* — Panitch Schwarze Belisario & Nadel LLP

(57) ABSTRACT

This invention includes agents and compositions having MRI, PET, CT, X-ray, SPECT or optical signals, and methods for their use in the determination of a target. In some cases, a MRI, PET, CT, X-ray, SPECT, optical or other signal produced by the agent or composition can be affected by the presence of the target. Examples of targets that can be determined by this invention include, but are not limited to zinc, copper, iron ions and other biological targets. Example of application for imaging in vivo includes the function of pancreas and other organs.

3 Claims, 12 Drawing Sheets

CONTRAST AGENTS

CROSS REFERENCE TO RELATED APPLICATIONS

This application claims benefit under 35 U.S.C. §119(e) of U.S. provisional application Ser. No. 61/225,187 filed on Jul. 13, 2009 which is incorporated herein by reference in its entirety.

TECHNICAL FIELD OF THE INVENTION

The present invention relates in general to the field of chelating agents, a method for preparing chelating agents and methods of using chelating agents in diagnostic and therapeutic applications.

BACKGROUND OF THE INVENTION

Without limiting the scope of the invention, its background is described in connection with contrast agents that detect a target in vivo for instance Zinc.

SUMMARY OF THE INVENTION

In one aspect, this invention relates to contrast agents for MRI, PET, CT, X-ray, SPECT, optical or ultrasound techniques consisting of a chelator group comprising a target binding unit, wherein the binding moiety is capable of binding a target further binding a protein in vivo such as human serum albumin and generating a signal that can be detected by MRI, PET, CT, X-ray, SPECT, optical or ultrasound techniques in vivo.

In another aspect, this invention also relates to compositions consisting of metal complexes of the chelator group wherein the metal complex has determinable signal by MRI, PET, CT, X-ray, SPECT, optical or ultrasound techniques wherein the binding target unit is capable of interacting with a target and further binding a protein in vivo such as human serum albumin generating a signal that can be detected MRI, PET, CT, X-ray, SPECT, optical or ultrasound techniques.

The present invention also relates to improved processes for the preparation of contrast agents consisting of a chelator group having a target binding unit.

Aspects of this invention include a MRI, PET, CT, X-ray, SPECT, optical or ultrasound agent or composition, having: a chelator group, a binding moiety covalently attached to the chelator group, wherein the binding moiety is capable of binding a target such that MRI, PET, CT, X-ray, SPECT, optical or ultrasound signal is changed upon binding the target, wherein the chelator group optionally comprises a metal, and wherein the agent is capable of detecting a target in vivo in a subject.

In some embodiments, the chelator group can include a macrocycle group containing at least nine atoms which at least three being heteroatoms; and the binding moiety can be N,N'-bis-2-pyridyl methyl amine (BPMA).

Yet in another aspect, the metal ion can be at least one paramagnetic metal such as $Gd^{3+}$, $Eu^{3+}$, $Tm^{3+}$, $Dy^{3+}$, $Tb^{3+}$, $Yb^{3+}$, $Mn^{2+}$, Ce, Pr, Nd, Pm, Sm, Ho, Er, Lu and Y. A radioactive metal such as $^{111}In^{3+}$, $^{113m}In^{3+}$, $^{67}Ga^{3+}$, $^{68}Ga^{3+}$, $^{99m}Tc^{4+}$, $^{64}Cu^{2+}$, $Tl^{3+}$, $^{153}Sm^{3+}$, $^{166}Ho^{3+}$ and $^{212}Bi^{3+}$, $^{90}Y^{3+}$, $^{377}Lu^{3+}$, $^{225}Ac^{3+}$, $^{149}Pm$, $^{159}Gd$, $^{140}La$, $^{175}Yb$, $^{47}Sc$, $^{186}Re$, $^{188}Re$, $^{97}Ru$, $^{105}Rh$, $^{109}Pd$, $^{197}Pt$, $^{67}Cu$, $^{198}Au$, $^{117m}Sn$, and $^{212}Pb$.

In some aspects, this invention includes an agent having the formula:

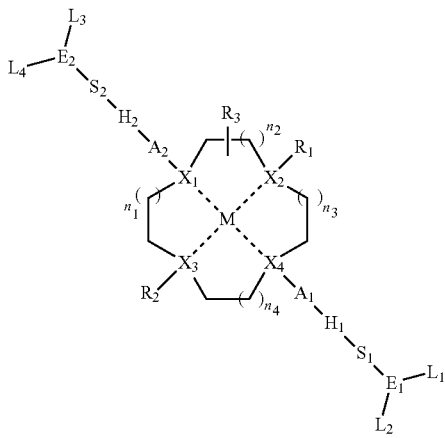

wherein $X_1$, $X_2$, $X_3$ and $X_4$ can be the same or different and each is a heteroatom preferably nitrogen.

In some aspects, M can be absent or if present M is a metal ion which can be used in MRI, PET, SPECT and optical, depending on the relaxometric, luminescent, fluorescent, or radioactive properties of the final form of the metal chelate contrast agent before and after binding to the relevant target. For example for diagnostic by MRI $Gd^{3+}$, $Eu^{3+}$, $Tm^{3+}$, $Dy^{3+}$, $Tb^{3+}$, $Yb^{3+}$ and $Mn^{2+}$ are preferred. For radiodiagnostic $^{111}In^{3+}$, $^{113m}In^{3+}$, $^{67}Ga^{3+}$, $^{68}Ga^{3+}$, $^{99m}Tc^{4+}$, $^{64}Cu^{2+}$, $Tl^{3+}$, or, for radiotherapy $^{153}Sm^{3+}$, $^{166}Ho^{3+}$ and $^{212}Bi^{3+}$, and more preferably, $^{90}Y^{3+}$, $^{377}Lu^{3+}$ and $^{225}Ac^{3+}$. Other metal ions in some embodiments for radiodiagnostic or radiotherapeutic applications include, but are not limited to: $^{149}Pm$, $^{159}Gd$, $^{140}La$, $^{175}Yb$, $^{47}Sc$, $^{186}Re$, $^{188}Re$, $^{97}Ru$, $^{105}Rh$, $^{109}Pd$, $^{197}Pt$, $^{67}Cu$, $^{198}Au$, $^{117m}Sn$, and $^{212}Pb$. Other metals can be Ce, Pr, Nd, Pm, Sm, Ho, Er, Lu or Y. $n_1$, $n_2$, $n_3$ and $n_4$ can be the same or different and each indicates a number of methylene ($CH_2$) units within the heterocyclic structure. These can be one, two, three or greater but preferably one.

Yet in other aspects, $R_1$ and $R_2$ can be the same or different and each is an acetate group, optionally this can be substituted in the methylene group. Alternatively, $R_1$ and $R_2$ can be an acetyl amide group which nitrogen can be substituted by an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ and $R_2$ can be an acetyl ester where the oxy substituent can be alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ and $R_2$ can include an organic compound having binding affinity for a cell surface receptor. Examples of such units comprise peptides, peptoids, or antibodies.

In some aspects, $R_3$ indicates a substituent or substituents in the methylene units of the macrocycle. These substituents can be of any chemical nature as described herein and if several they can be the same or different. $A_1$ and $A_2$ can be the same or different and each indicates an acetyl group preferably, optionally this can be substituted in the methylene group. $H_1$ and $H_2$ can be the same or different and each indicates a heteroatom preferably nitrogen. $S_1$ and $S_2$ can be the same or different and each indicates an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $S_1$ and $S_2$ might not be present. $E_1$ and $E_2$ can be the same or different and each indicates a heteroatom preferably nitrogen. Alternatively, $E_1$ and $E_2$ might not be present. $L_1$, $L_2$, $L_3$ and $L_4$ can be the same or different and each comprises a target binding moiety which upon binding the target can bind another molecule further for example a protein. $L_1$, $L_2$, $L_3$ and $L_4$ can be a substituted derivative of a heterocycle unit such as but not limited to pyridine, pyrazole, imidazole, piperidine, pyrazine, pyrimidine, pyrrol. Alternatively, $L_1$, $L_2$, $L_3$ and $L_4$ can be an alkyl, alkenyl, alkynyl, cycloalkyl, cycloalkenyl, cycloalkynyl, heteroalkyl, heteroalkenyl, heteroalkynyl or aryl optionally substituted.

In one aspect, the agent has the formula:

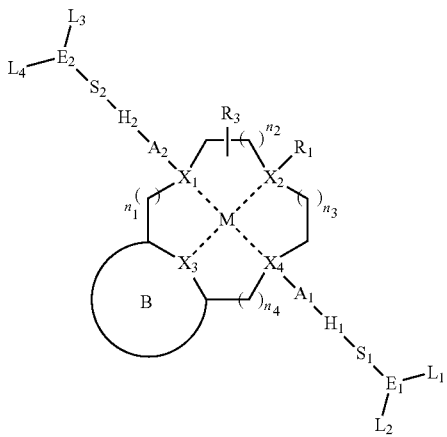

where B includes a cyclic compound within the macrocycle including one heteroatom of the macrocycle. This cyclic moiety can be aliphatic or aromatic with or without heteroatoms other than the one in the macrocycle, optionally the cycle might be substituted.

Yet in another aspect, agent has the formula:

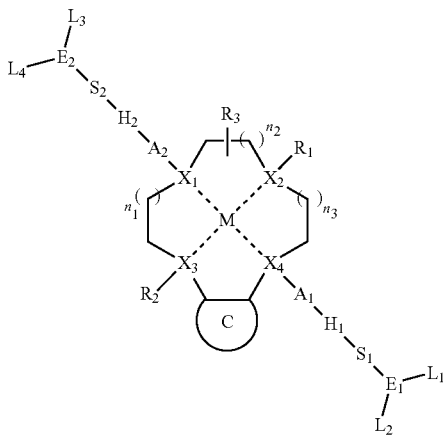

where C includes a cyclic compound within the macrocycle. This cyclic moiety can be aliphatic or aromatic with or without heteroatoms, optionally substituted.

Yet in another aspect, agent has the formula:

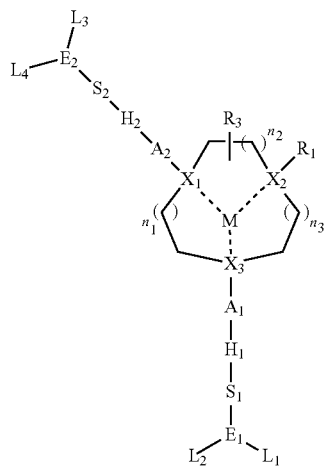

wherein: $X_1$, $X_2$, and $X_3$ can be the same or different and each is a heteroatom nitrogen. M can be absent or if present M is a metal ion which could be used in MRI, PET, SPECT or optical, depending on the relaxometric, luminescent, fluorescent, or radioactive properties of the final form of the metal chelate contrast agent before and after binding to the relevant target. For example for diagnostic by MRI $Gd^{3+}$, $Eu^{3+}$, $Tm^{3+}$, $Dy^{3+}$, $Tb^{3+}$, $Yb^{3+}$ or $Mn^{2+}$. For radiodiagnostic $^{111}In^{3+}$, $^{113m}In^{3+}$, $^{67}Ga^{3+}$, $^{68}Ga^{3+}$, $^{99m}Tc^{4+}$, $^{64}Cu^{2+}$, $Tl^{3+}$, or for radiotherapy $^{153}Sm^{3+}$, $^{166}Ho^{3+}$ and $^{212}Bi^{3+}$, and, $^{90}Y^{3+}$, $^{377}Lu^{3+}$ and $^{225}Ac^{3+}$. Other metal ions for radiodiagnostic or radiotherapeutic applications include, but are not limited to: $^{149}Pm$, $^{159}Gd$, $^{140}La$, $^{175}Yb$, $^{47}Sc$, $^{186}Re$, $^{188}Re$, $^{97}Ru$, $^{105}Rh$, $^{109}Pd$, $^{197}Pt$, $^{67}Cu$, $^{198}Au$, $^{117m}Sn$, or $^{212}Pb$. Other metals can be Ce, Pr, Nd, Pm, Sm, Ho, Er, Lu or Y. $n_1$, $n_2$, and $n_3$ can be the same or different and each indicates a number of methylene ($CH_2$) units within the heterocyclic structure. These can be one, two, three or greater but preferably one. $R_1$ is an acetate group, optionally this can be substituted in the methylene group. Alternatively, $R_1$ can be an acetyl amide group which nitrogen can be substituted by an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ can be an acetyl ester where the oxy substituent can be alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ can comprise an organic compound having binding affinity for a cell surface receptor. Examples of such units comprise peptides, peptoids, or antibodies. $R_3$ indicates a substituent or substituents in the methylene units of the macrocycle. These substituents can be of any chemical nature as described herein and if several they can be the same or different. $A_1$ and $A_2$ can be the same or different and each indicates an acetyl group preferably, optionally this can be substituted in the methylene group. $H_1$ and $H_2$ can be the same or different and each indicates a heteroatom preferably nitrogen. $S_1$ and $S_2$ can be the same or different and each indicates an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $S_1$ and $S_2$ might not be present. $E_1$ and $E_2$ can be the same or different and each indicates a heteroatom preferably nitrogen. Alternatively, $E_1$ and $E_2$ might not be present. $L_1$, $L_2$, $L_3$ and $L_4$ can be the same or different and each comprises a target binding moiety which upon binding the target can bind another molecule further for example a protein. $L_1$, $L_2$, $L_3$ and $L_4$ can be a substituted derivative of a heterocycle unit such as but not limited to pyridine, pyrazole, imidazole, piperidine, pyrazine, pyrimidine, pyrrol. Alternatively, $L_1$, $L_2$, $L_3$ and $L_4$ can be an alkyl, alkenyl, alkynyl, cycloalkyl, cycloalkenyl, cycloalkynyl, heteroalkyl, heteroalkenyl, heteroalkynyl or aryl optionally substituted.

In some aspects, the agent of this invention can have the structure:

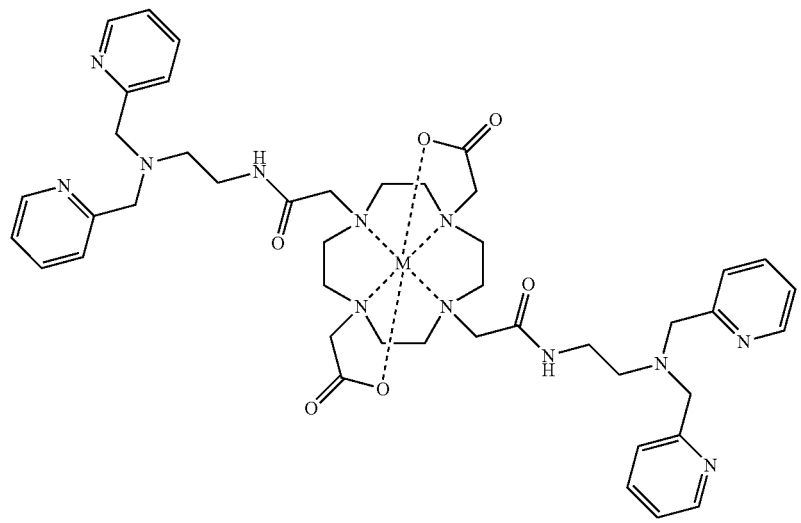

where in: M is $Gd^{3+}$, $Eu^{3+}$, $Tm^{3+}$, $Dy^{3+}$, $Tb^{3+}$, $Yb^{3+}$, $Mn^{2+}$, Ce, Pr, Nd, Pm, Sm, Ho, Er, Lu or Y. At least one radioactive metal such as $^{111}In^{3+}$, $^{113m}In^{3+}$, $^{67}Ga^{3+}$, $^{68}Ga^{3+}$, $^{99m}Tc^{4+}$, $^{64}Cu^{2+}$, $Tl^{3+}$, $^{153}Sm^{3+}$, $^{166}Ho^{3+}$ and $^{212}Bi^{3+}$, $^{90}Y^{3+}$, $^{377}Lu^{3+}$ and $^{225}Ac^{3+}$ $^{149}Pm$, $^{159}Gd$, $^{140}La$, $^{175}Yb$, $^{47}Sc$, $^{186}Re$, $^{188}Re$, $^{97}Ru$, $^{105}Rh$, $^{109}Pd$, $^{197}Pt$, $^{67}Cu$, $^{198}Au$, $^{117m}Sn$, or $^{212}Pb$.

In one aspect, the target is a metal ion for instance $Zn^{2+}$ or $Cu^{2+}$ or macromolecular receptor such as a protein.

Yet in another aspect, this invention include a process for making an agent as where the chelator unit is covalently attached to the binding unit with a coupling agent and a base, wherein said coupling agent can be an uronium-containing compound or a phosphonic acid cyclic anhydride for instance wherein said can be O-Benzotriazole-N,N,N',N'-tetramethyl-uronium-hexafluoro-phosphate or 1-propanephosphonic cyclic anhydride. The method can further include cleaving said of ester groups in presence of an acid to form carboxylic acids, wherein said acid can be hydrochloric acid or trifluoroacetic acid.

In one aspect, this invention includes a method of generating images of an animate human or non-human subject involving administering a contrast agent to said subject and generating an image of at least a part of the said subject to which said contrast agent has distributed, accumulated and or bound to the target, characterized in that as said contrast agent is used as matter of formula. In one aspect, the image is a magnetic resonance image (MRI), a nuclear imaging image, an ultrasound image, or an optical image.

In some aspects, the levels of a target in a given image can be determined by administering a low concentration of the agent or composition such as in the micromolar range for MRI and nanomolar or lower with other nuclear imaging techniques that involving radionuclides, and that the concentration of the agent or composition is such that its signal in an image is zero/baseline background without significant target concentration.

Yet in another aspect, this invention includes a pharmaceutical composition having a composition of matter of formula together with at least one pharmaceutically effective carrier or excipient.

Yet in another aspect, the present invention include a method of making the novel composition comprising attaching the chelator unit covalently to the binding unit using a coupling agent and with a base dissolved in a solvent, wherein the coupling agent comprises a uronium-containing compound, and wherein said solvent comprises polar aprotic solvents; and treating the resultant purified product with an acid to cleave ester groups to form carboxylic acids. The coupling agent comprises a phosphonic acid cyclic anhydride; and wherein said bases are non-nucleophilic organic tertiary amines or non-nucleophilic inorganic bases.

In another aspect, the present invention includes a method of generating images of an animate human or non-human subject comprising administering a contrast agent to said subject; and generating an image of at least a part of said subject to which said contrast agent has distributed, accumulated or bound to the target wherein said image is a magnetic resonance (MRI), nuclear, ultrasound or optical image.

In another aspect, the present novel composition can be used as a pharmaceutical composition comprising the composition of matter of formula as defined in claim 1 together with at least one pharmaceutically effective carrier or excipient.

BRIEF DESCRIPTION OF THE DRAWINGS

For a more complete understanding of the features and advantages of the present invention, reference is now made to the detailed description of the invention along with the accompanying figures and in which.

Figure 1:
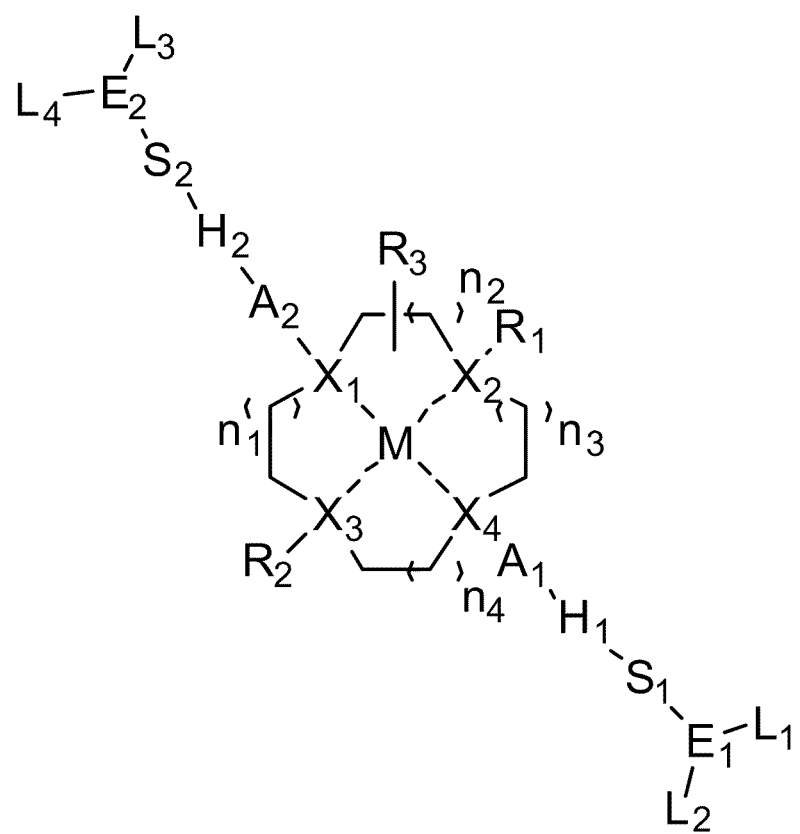
FIG. 1 shows a general formula for a class of tetraheterocyclic-based agents, according to some embodiments of the invention.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example can be used for illustration. The terminology herein is used to describe specific embodiments of the invention, but their usage does not delimit the invention, except as outlined in the claims.

As used herein, the term in vivo describes living organisms such as animals and humans.

A used herein, "signal shift" refers to an alteration on the detected signal obtained by MRI, PET, SPECT, optical and ultrasound apparatus given the presence of an agent or composition, the specific binding of the agent to a target and further binding to a macromolecule. Examples are changes in the relaxometric, luminescent, fluorescent, or radioactive properties of the agent which translate in changes on signal intensities of the detected signals by MRI, PET, SPECT, optical and ultrasound techniques.

As used herein the term "determining" generally refers to the analysis of a species or signal, for example quantitatively or qualitatively, and/or the detection of the presence or absence of the species signals. "Determining" can also refer to the analysis of an interaction between two or more species or signals.

As used herein, the term "paramagnetic metal ion" describes a metal ion having unpaired electrons, causing the metal ion to have a measurable magnetic moment in the presence of an externally applied field. Examples of suitable paramagnetic metal ions, include, but are not limited to, ions of iron, nickel, manganese, copper, gadolinium, dysprosium, europium, and the like. In some embodiments, an agent or composition of this invention, can have a chelator group bound to a paramagnetic metal ion, wherein the paramagnetic ion is $Gd^{3+}$.

As used herein, an emission's can be a luminescence emission, in which "luminescence" is defined as an emission of ultraviolet or visible radiation. Specific types of luminescence include, but are not limited to, fluorescence, phosphorescence, chemiluminescence, electrochemiluminescence, and the like. In some cases, the emission can be fluorescence emission.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl can have 30 or fewer carbon atoms knits backbone, and, in some cases, 20 or fewer e.g., 19, 18, 17, 16, 15, 14, 13, 12, 11, 10, 9, 8, 7, 6, 5, 4, 3, 2 or 1. In some embodiments, a straight chain or branched chain alkyl has 12 or fewer carbon atoms in its backbone. Yet in another embodiments 6 or fewer, and 4 or fewer. Likewise, cycloalkyls have from 3-10 carbon atoms in their ring structure, and can have 5, 6 or 7 carbons in the ring structure. Examples of alkyl groups include, but are not limited to, methyl, ethyl, propyl, isopropyl, cyclopropyl, butyl, isobutyl, tell-butyl, cyclobutyl, hexyl, cyclohexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, and the like.

The terms "alkenyl" and "alkynyl" refer to unsaturated aliphatic groups analogous in length and possible substitution to the alkyls described above, but that contained at least one double or triple bond respectively.

The terms 'heteroalkenyl" and 'heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "acetyl group" are recognized in the art and can include such moieties as can be represented by the general formula: —C(=O)G, where if G is OH the formula represents an acetate; if G is O—P where P can be alkyl, alkenyl, alkynyl, cycloalkyl, cycloalkenyl, cycloalkynyl, heteroalkyl, heteroalkenyl, heteroalkynyl, aryl or heterocycle the formula represents acetyl esters and N—P where P can be alkyl, alkenyl, alkynyl, cycloalkyl, cycloalkenyl, cycloalkynyl, heteroalkyl, heteroalkenyl, heteroalkynyl, aryl or heterocycle the formula represents acetyl amides, where alkyl, alkenyl, alkynyl, cycloalkyl, cycloalkenyl, cycloalkynyl, heteroalkyl, heteroalkenyl, heteroalkynyl, aryl or heterocycle are the substituents in the nitrogen or oxy part of the acetyl group.

The term "aryl" refers to aromatic carbocyclic groups, optionally substituted, having a single ring (e.g., phenyl), multiple rings (e.g., biphenyl), or multiple fused rings in which at least one is aromatic (e.g. naphthyl, antryl, or phenanthryl). That is, at least one ring can have a conjugated pi electron system, while other, adjoining rings can be cycloalkyls, cycloalkenyls, cycloalkynyls, aryls and/or heterocycles.

The term "macrocycle" refers to cyclic groups containing three or four heteroatoms in their structure with the remainder of the ring of the ring being carbon atoms at least 6.

The term "heterocycle" refers to cyclic groups containing at least one heteroatom as a ring atom, in some cases, 1, 2 to 3 heteroatoms as ring atoms, with the remainder of the ring atoms being carbon atoms. Suitable heteroatoms include oxygen, sulfur, nitrogen, phosphorus, and the like. In some cases, the heterocycle can be 3-, 4-, 5-, 6-, 7-, 8-, 9- to 10-membered ring structures. Yet in another embodiment, 3- to 7-membered rings, whose ring structures include one to four heteroatoms. The term "heterocycle" can include heteroaryl groups (e.g., aromatic heterocycles), saturated heterocyclic (e.g., cycloheteroalkyl) groups, or combinations thereof. The heterocycle can be a saturated molecule, or can comprise one or more double bonds. In some case, the heterocycle is an aromatic heterocycle, such as pyrrole, pyridine, and the like. In some cases, the heterocycle can be attached to, or fused to, additional rings to form a polycyclic group. In some cases, the heterocycle can be part of a macrocycle. The heterocycle can also be fused to a spirocyclic group. In some cases, the heterocycle can be attached to a compound via a nitrogen or a carbon atom in the ring. Heterocycles include, for example, thiophene, benzothiophene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazine, piperidine, homopiperidine, piperazine, morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle can be bonded to a compound via a heteroatom ring atom (e.g., nitrogen). In some cases, the heterocycle can be bonded to a compound via a carbon ring atom.

As used herein the terms "amine" and "amino" describes both unsubstituted and substituted amines, e.g., a moiety that can be represented by the general formula: N(R')(R")(R''') wherein R' R" and R''' each independently represent a group permitted by the rules of valence.

Any of the above groups can be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination. In some cases, "substituted" can refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and subbranches, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen can have hydrogen substituent and/or any permissible substituents of organic compounds described herein which satisfy the valencies of the heteroatoms. Examples of substituents include, but aren't limited to, halogen, azide, alkyl, aralkyl, alkenyl, alkynyl, cycloalkyl, hydroxyl, alkoxyl, amino, nitro, sulfhydryl, amino, amide, phosphonate, phosphinate, carbonyl, carboxyl, silyl, ether, alkylthio, sulfonyl, sulfonamide, ketone, aldehyde, ester, heterocyclyl, aromatic or heteroaromatic moieties, —CF$_3$, —CN, aryl, aryloxy, perhaloalkoxy, aralkoxy, heteroaryl, heteroaryloxy, heteroarylalkyl, heteroaralkoxy, azido, halide, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylylaminoalkylcarboxy-, aminocarboxamidoalkyl-, alkoxyalkyl, perhaloalkyl, arylalkyloxyalkyl, and the like.

In other embodiments, this invention also relates to compounds having MRI, PET, CT, X-ray, SPECT, optical or ultrasound signals and their use in the analysis of the location, presence, ad/or quantity of a particular target in vivo. In some embodiments, agents or compositions are provided to be detectable in a MRI, PET, CT, X-ray, SPECT, optical or ultrasound apparatus. In some cases the MRI, PET, CT, X-ray, SPECT, optical or other signal produced by the agent can be affected by the presence of a particular target. The use of such agents can facilitate the study of the physiological roles of species including, for example zinc ($Zn^{2+}$), copper ($Cu^{2+}$), iron ($Fe^{2+}$ or $Fe^{3+}$) or other targets and can aid in the diagnostic and therapy of pathological conditions.

Another advantage of the present invention relates to the capability to synthesize a broad variety of agents and compositions with different signal detections properties (e.g. MRI, PET, CT, X-ray, SPECT, optical, ultrasound based detection) and designed to specifically interact with a particular target. For example, the invention can involve the synthesis of an agent that suits several applications. In some cases, the agent can be bound to a metal ion which determines the mechanism of detection by which the agent determines the target. In an example embodiment the invention can comprise the synthesis of an agent which can be used as an optical based agent. Further binding of the same molecular unit to a paramagnetic or radioactive metal ion can then produce an MRI, PET, CT, X-ray, SPECT based agent. In another variation the molecular platform bound to a paramagnetic metal might be used as an optical and MRI agent. Depending on the paramagnetic metal the molecular platform can be used as a T1, T2 and/or PARACEST contrast agent. The molecular platform can also comprise one or more attachment sites for various binding moieties selected to specifically interact with a target.

In some embodiments, the present invention provides methods for determination of a target, such as $Zn^{2+}$, $Cu^{2+}$ and/or other biological targets. The agent or composition can comprise a chelator group having an MRI, PET, CT, X-ray, SPECT, optical or ultrasound signal and a binding moiety covalently attached to the chelator group for binding a target.

The localization and determination of the target such as $Zn^{2+}$ in vivo is based on the localization of the agent as total signal or by time-course analysis of the agents' retention in a particular site of the body. Alternatively, determination of the target can comprise exposing the agent or composition to a sample suspected containing the target. If present, the target can interact with the agent to produce a particular MRI, PET, CT, X-ray, SPECT, optical or ultrasound signal of the agent or composition.

In some embodiments, the present invention provides methods for imaging particular locations within a living organism. The agent or composition comprise of a chelator group having an MRI, PET, CT, X-ray, SPECT, optical or ultrasound signal and a binding moiety covalently attached to the chelator group. Where the agent or composition presents a preferred accumulation in a particular location within a living organism, which allows the detection of a signal by MRI, PET, CT, X-ray, SPECT, optical or ultrasound apparatus. In some embodiments such accumulation might be due to interaction of the agent or composition with a target. In another embodiment the accumulation can be directed by the interaction of the agent or composition with another molecule different to the target given that the agent or composition might also interact with the target.

As described herein agents or compositions can comprise a chelator group and a binding moiety covalently attached to the chelator group. The chelator group can be capable of binding a metal ion such as a paramagnetic or radioactive metal ion and the binding moiety can be capable of binding a target. As described herein, the presence of a metal ion bound to the chelator group, or the type of metal ion bound to the chelator group, can affect one or more properties of the agent, such as an MRI, PET, CT, X-ray, SPECT, optical or ultrasound property. In some cases, the agent can be capable of binding a target and the presence of the target can affect one or more properties of the agent. In some cases, when the agent binds the target it can bind another molecule (for example human serum albumin) and the presence of these molecule can affect one or more properties of the agent.

The agents described herein bind to a target for instance $Zn^{2+}$ and then could associate and/or bind with the ubiquitous serum albumin to form a complex and with increased longitudinal relaxivity, become more useful for MRI. The association of the agent with the relevant metals will allow for the delineation and localization of the sites where the target metal is released, retarded, accumulated or trapped, thus allowing for MRI, PET, SPECT or optical detection depending on the composition of the metal center of the contrast agent, whether MRI active, optically traceable, radioactive or not.

Figure 2:
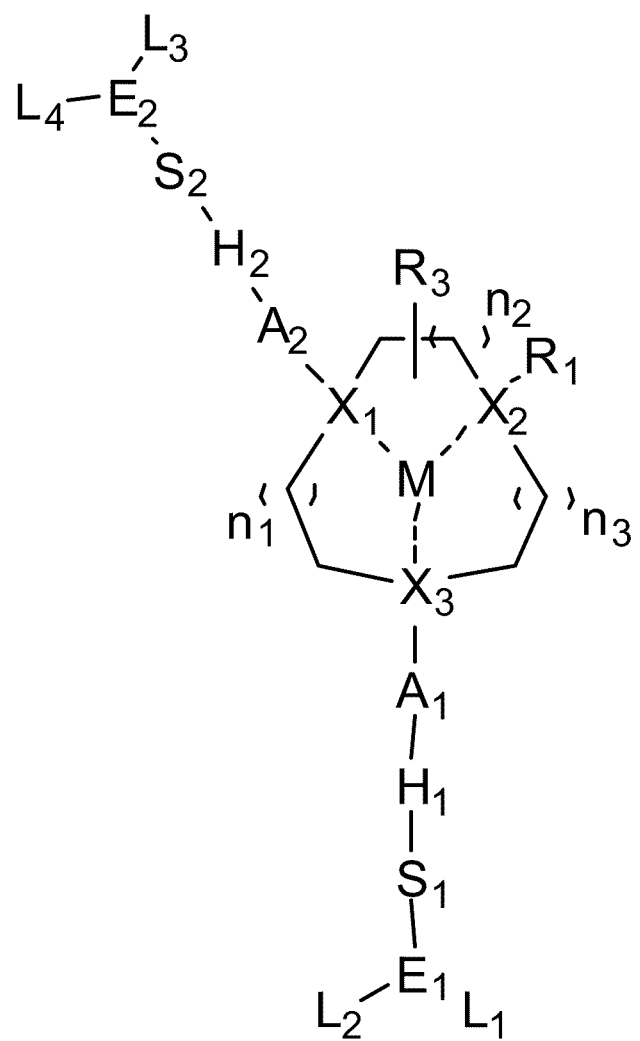
FIG. 2 shows a general formula for a class of triheterocyclic-based agents, according to some embodiments of the invention.
Figure 3:
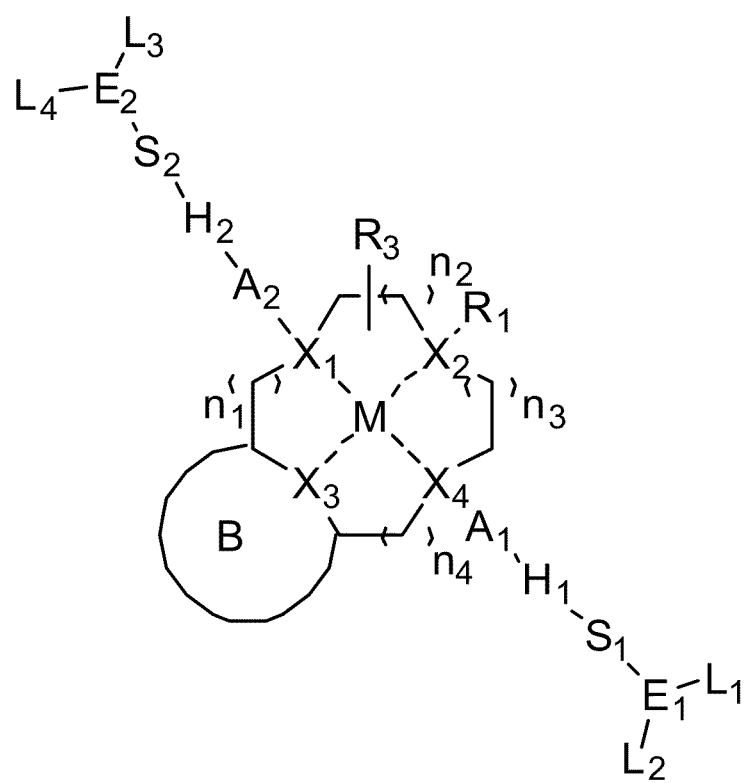
FIG. 3 shows a general formula for a class of tetraheterocyclic-based agents containing an external cyclic moeity, according to some embodiments of the invention.
Figure 4:
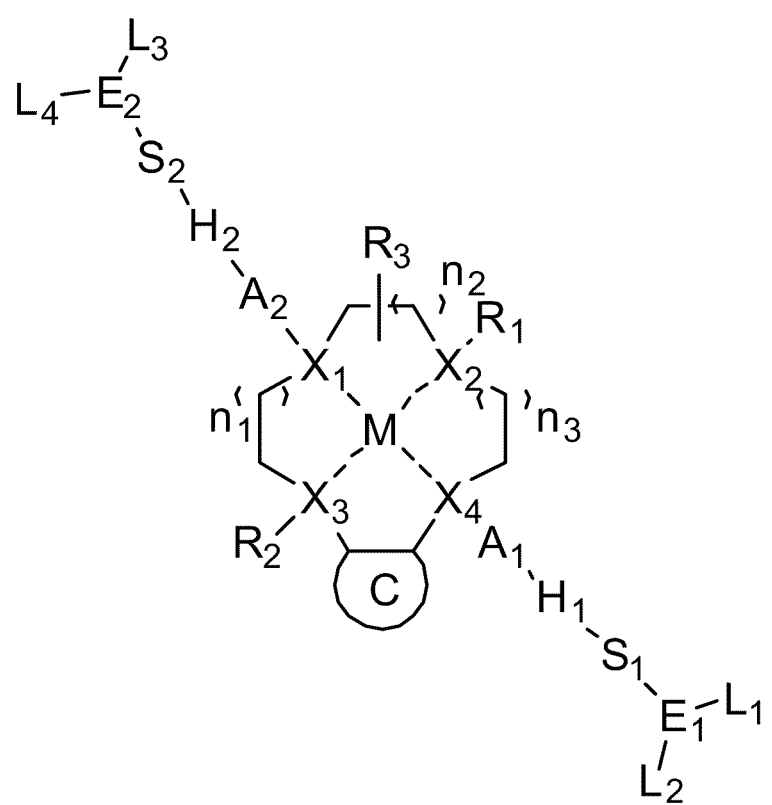
FIG. 4 shows a general formula for a class of tetraheterocyclic-based agents containing an external cyclic moeity, according to some embodiments of the invention.

In some cases, the chelator group comprises of three or more heteroatoms within a cyclic structure herein called macrocycle, which can coordinate a metal ion as shown in FIGS. 1, 2, 3 and 4. The heteroatoms can be nitrogen, oxygen, sulfur, etc. with nitrogen being preferred. In some embodiments, the chelator comprises at least three, at least four heteroatoms or greater. In some cases as depicted in FIGS. 3 and 4, the chelator group contains at least one cycle within the macrocycle.

Some agents or compositions of the invention can further comprise a binding moiety covalently attached to the chelator capable of binding a target. In some cases, the binding moiety might comprise one or more groups capable of interacting with the target which in combination might further interact with another molecule. In some embodiments, the binding moiety can comprise one or more heteroatoms capable of binding a metal ion or other species present with a living organism (e.g. animal, human). In some embodiments, the binding unit is N,N'-bis-2-pyridyl methyl amine (BPMA).

Some embodiments of the invention comprise an agent having the formula shown in FIG. 1 and FIG. 2, wherein: $X_1$, $X_2$, $X_3$ and $X_4$ can be the same or different and each is a heteroatom preferably nitrogen. M can be absent or if present M is a metal ion which could be used in MRI, PET, SPECT and optical, depending on the relaxometric, luminescent, fluorescent, or radioactive properties of the final form of the metal chelate contrast agent before and after binding to the relevant target. For example for diagnostic by MRI $Gd^{3+}$, $Eu^{3+}$, $Tm^{3+}$, $Dy^{3+}$, $Tb^{3+}$, $Yb^{3+}$ and $Mn^{2+}$. For radiodiagnostic $^{111}In^{3+}$, $^{113m}In^{3+}$, $^{67}Ga^{3+}$, $^{68}Ga^{3+}$, $^{99m}Tc^{4+}$, $^{64}Cu^{2+}$, Tl3+, or, for radiotherapy $^{153}Sm^{3+}$, $^{166}Ho^{3+}$ and $^{212}Bi^{3+}$, and $^{90}Y^{3+}$, $^{377}Lu^{3+}$ and $^{225}Ac^{3+}$. Other metal ions for radiodiagnostic or radiotherapeutic applications include: $^{149}Pm$, $^{159}Gd$, $^{140}La$, $^{175}Yb$, $^{47}Sc$, $^{186}Re$, $^{188}Re$, $^{97}Ru$, $^{105}Rh$, $^{109}Pd$, $^{197}Pt$, $^{67}Cu$, $^{198}Au$, $^{117m}Sn$, and $^{212}Pb$. Other metals can be Ce, Pr, Nd, Pm, Sm, Ho, Er, Lu and Y. $n_1$, $n_2$, $n_3$ and $n_4$ can be the same or different and each indicates a number of methylene ($CH_2$) units within the heterocyclic structure. These can be one, two, three or greater but preferably one. $R_1$ and $R_2$ can be the same or different and each is an acetate group preferably, optionally this can be substituted in the methylene group. Alternatively, $R_1$ and $R_2$ can be an acetyl amide group which nitrogen can be substituted by an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ and $R_2$ can be an acetyl ester where the oxy substituent can be alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $R_1$ and $R_2$ can comprise an organic compound having binding affinity for a cell surface receptor. Examples of such units comprise peptides, peptoids, antibodies. $R_3$ indicates a substituent or substituents in the methylene units of the macrocycle. These substituents can be of any chemical nature as described herein and if several they can be the same or different. $A_1$ and $A_2$ can be the same or different and each indicates an acetyl group preferably, optionally this can be substituted in the methylene group. $H_1$ and $H_2$ can be the same or different and each indicates a heteroatom preferably nitrogen. $S_1$ and $S_2$ can be the same or different and each indicates an alkyl, alkenyl, alkynyl, cycloalkyl, cycloalkenyl, cycloalkynyl, heteroalkyl, heteroalkenyl, heteroalkynyl, aryl or heterocycle unit optionally substituted. Alternatively, $S_1$ and $S_2$ might not be present. $E_1$ and $E_2$ can be the same or different and each indicates a heteroatom preferably nitrogen. Alternatively, $E_1$ and $E_2$ might not be present. $L_1$, $L_2$, $L_3$ and $L_4$ can be the same or different and each comprises a target binding moiety which upon binding the target can bind another molecule further for example a protein. $L_1$, $L_2$, $L_3$ and $L_4$ can be a substituted derivative of a heterocycle unit such as but not limited to pyridine, pyrazole, imidazole, piperidine, pyrazine, pyrimidine, pyrrol. Alternatively, $L_1$, $L_2$, $L_3$ and $L_4$ can be an alkyl, alkenyl, alkynyl, cycloalkyl, cycloalkenyl, cycloalkynyl, heteroalkyl, heteroalkenyl, heteroalkynyl or aryl optionally substituted.

In some embodiments of the invention, the agent has the formula shown in FIG. 2, wherein: B comprises a cyclic compound within the macrocycle including one heteroatom of the macrocycle. This cyclic moiety can be aliphatic or aromatic with or without heteroatoms other than the one in the macrocycle, optionally the cycle might be substituted.

In some embodiments of the invention, the agent has the formula shown in FIG. 3, wherein: C includes a cyclic compound within the macrocycle. This cyclic moiety can be aliphatic or aromatic with or without heteroatoms, optionally substituted.

Agents of the present invention can be synthesized using a variety of known methods. In some cases, synthesis of an agent can comprise attachment of the chelator group to one or more binding moieties as in $E_1$-$L_1$(-$L_2$), $E_2$-$L_3$(-$L_4$), optionally via a linker comprising the units $H_1$—$S_1$-$E_1$-$L_1$(-$L_2$), $H_2$—$S_2$-$E_2$-$L_3$(-$L_4$) using a coupling reagent. The chelator group can comprise at least one functional group capable of forming a bond with a binding moiety, or linker for binding moiety.

An important class of chelators included in some embodiments of the invention are based on tetraaza macrocycle units, for example 1, 4,7,10-tetraazacyclododecane (cyclen) which are usually functionalized in the secondary amines with electrophilic compounds such as halide containing reagents. However, these processes are deficient giving final products in poor to moderate yields. Among the problems associated when using halide containing reagents are intra- or inter amine quaternization when preparing or using halide compounds comprising a tertiary amine in their structure such as the case of BPMA unit discussed in some embodiments of the present invention. Additionally, incomplete macrocycle secondary amine substitution occurs when bulky haloacetylamide derivatives are used. Those of ordinary skill in the art will understand the meaning of these terms. A way to solve these problems from previous states of the art and as an embodiment of the present invention is to use macrocycle derivatives which contain the heteroatom preferably nitrogen substituted with an acetate group. Alternatively, some of the carboxylic acids of the acetates, one, preferably two or three might be substituted as described herein, if forming an ester as described a tert-butyl ester is preferred. Examples comprise 1,4,7,10-tetraazacyclododecane-1,4,7,10-tetracetic acid (DOTA), DOTA-bis-tert-butyl ester and derivatives as described herein. Another embodiment of the invention comprises the direct attachment of the binding moiety to the acetate units of the chelator. Any conventional method can be used to produce DOTA and derivatives for example the synthesis of DOTA-bis-tert-butyl ester has been described in the Mexican Patent application GT/a/2004/000018 by L. M. De León-Rodríguez and Z. Kovacs and DOTA synthesis was described by J. F. Desreux, *Inorg. Chem.* 19(5): 1319-24 (1980). Both references incorporated herein. Alternatively, such compounds are commercially available.

The coupling agent can include any conventional compound known by those skilled in the art to facilitate the coupling of the binding unit to the chelator. In particular uronium/guanidium or uronium-containing coupling reagents or phosphonic acid cyclic anhydrides can be used. In certain embodiments, for example, the coupling agent is 2-(1H-Benzotriazole-1-yl)1,1,3,3-tetramethyluronium hexafluorophosphate (HBTU) in either N- or O- form. The term N- or O- form as used herein, refer to the atoms, either nitrogen or oxygen, directly involved in forming the covalent linkage between the benzotriazole group and the tetramethyluronium group. In other embodiments, for example, the coupling agent is 1-propanephosphonic cyclic anhydride. Such compounds are available from commercial sources.

In one embodiment, the chelator, coupling agent and binding unit are combined in a solvent capable of dissolving these compounds to form a homogeneous mixture. It is advantageous for the solvent to be an aprotic organic solvent, such as dimethylformamide. Alternatively, a base can be added to the homogeneous mixture. Preferred bases are non-nucleophilic tertiary amines for example N,N,N'-diisopropylethylamine, trietylamine or alternatively inorganic bases such as alkaline metal carbonates or bicarbonates for example sodium carbonate. The molar ratio chelator, coupling agent, binding unit and alternatively base in the mixture is about 1:1 times the number of acetate arms in the chelator:1 times the number of acetate arms in the chelator:2 times the number of acetate arms in the chelator. The reaction is preferably carried out by maintaining the solution containing the chelator, coupling agent, binding unit and base at a constant temperature with stirring for about 2 to about 24 hours (e.g., about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours) to allow attachment of the chelator to the binding unit. The reaction can be carried out at any temperature where the mixture remains in liquid state; from about −10° C. to about 50° C. (e.g., −5° C., 0° C., 5° C., 10° C., 15° C., 20° C., 25° C., 30° C., 35° C., 40° C., 45° C.), or at about room temperature (e.g., about 22° C.).

After the reaction period, the organic solvent is removed by conventional techniques, such as vacuum evaporation at about 40° C. The residual reaction mixture is dissolved in an organic solvent, such as dichloromethane and is washed multiple times with water which might contain sodium hydroxide about 0.1 M to about 0.3 M. The washing steps are preferably carried out in a reparatory funnel to facilitate removal of the washing solvent.

Next the organic phase is transferred to another vessel and a hydroscopic salt, such as sodium sulfate is added to the vessel to remove residual water. The mixture is filtered, for example in a sintered glass filter. The filtrate is collected and solvent removed by conventional techniques. The residual product contains the contrast agent which might be further purified by if needed.

If tert-butyl groups are present in the final product this can be removed following ordinary procedures. For instance the agent containing tert-butyl groups can be dissolved in HCl 1M in water and stirred at room temperature for 2 hours. Solvent can then be removed by ordinary techniques.

Figure 5:
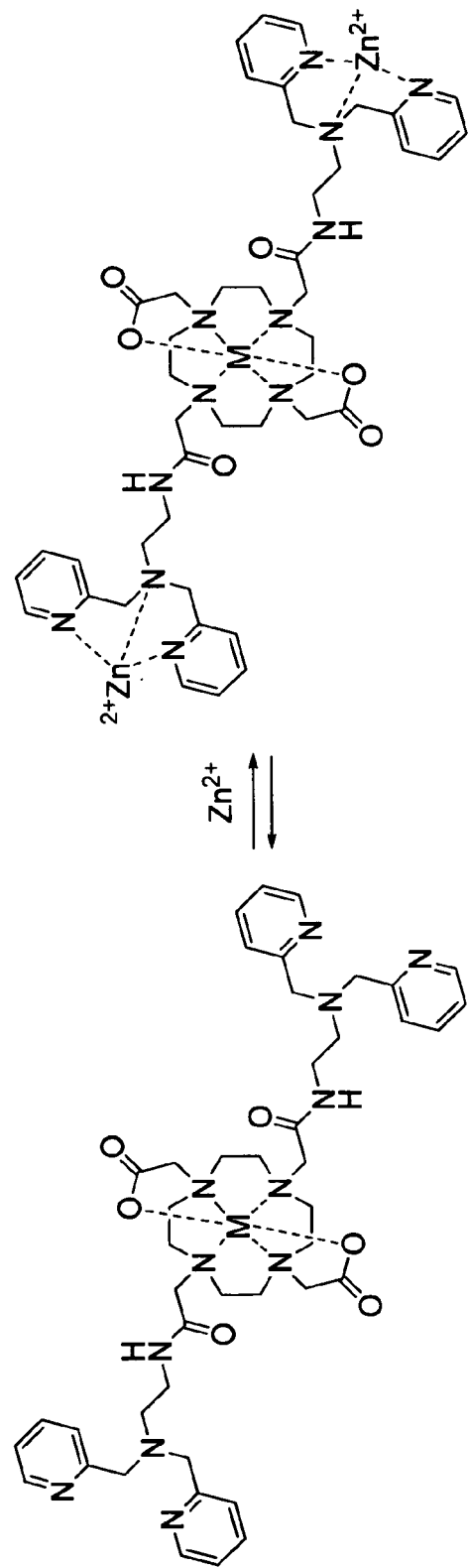
FIG. 5 shows a tetraazaheterocyclic agent named herein DOTA-diBPMA that can be useful in the determination of a target for example $Zn^{2+}$ by MRI, PET, CT, X-ray, SPECT or optical apparatus depending on M.
Figure 6:
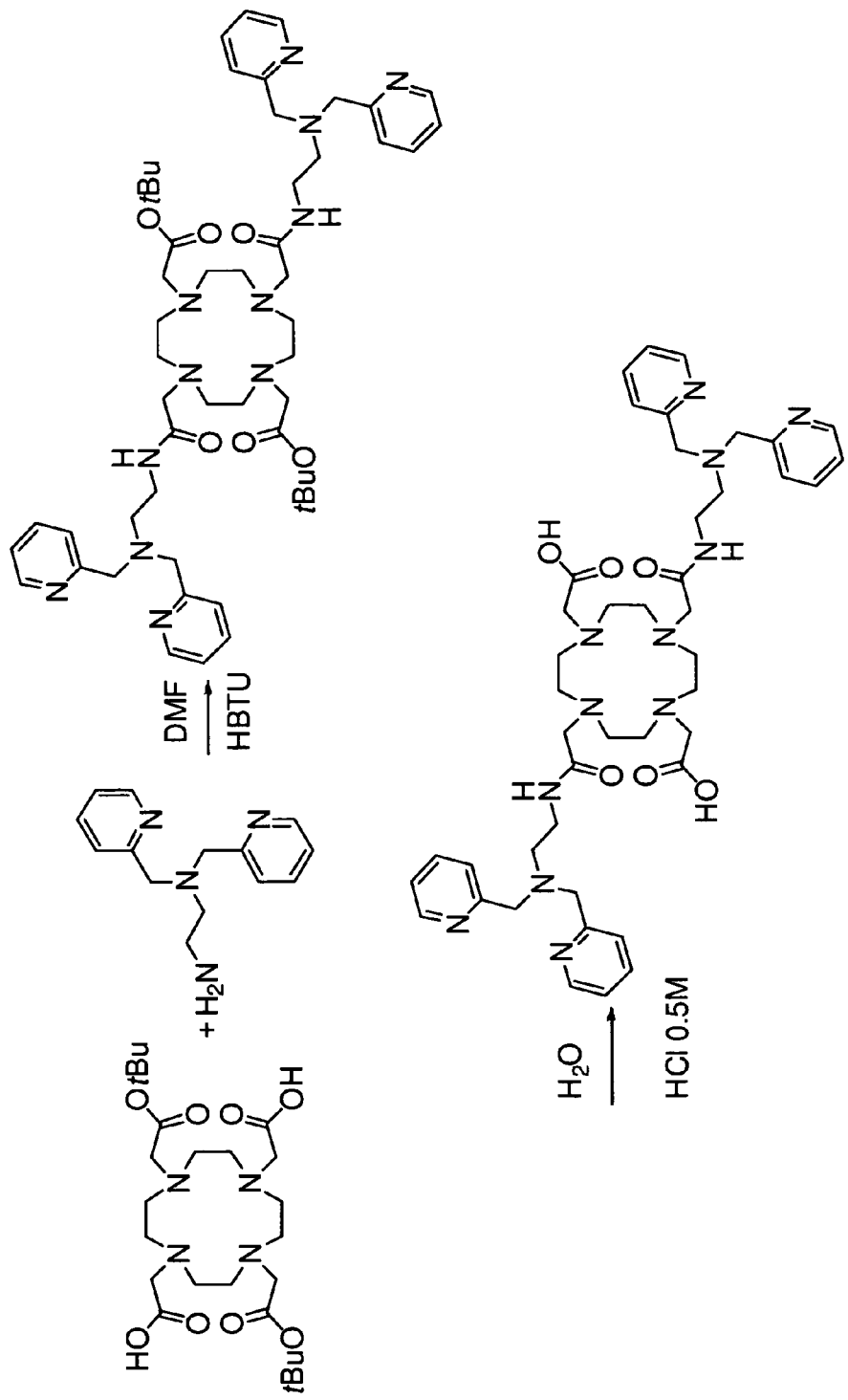
FIG. 6 shows the synthesis of an agent that comprises as a chelator a 1,4,7,10-tetraazacyclododecane unit substituted in the nitrogen atoms with acetate and acetyl units which is then bound to a target binding unit named herein BPMA, according to one embodiment of the invention.
Figure 7:
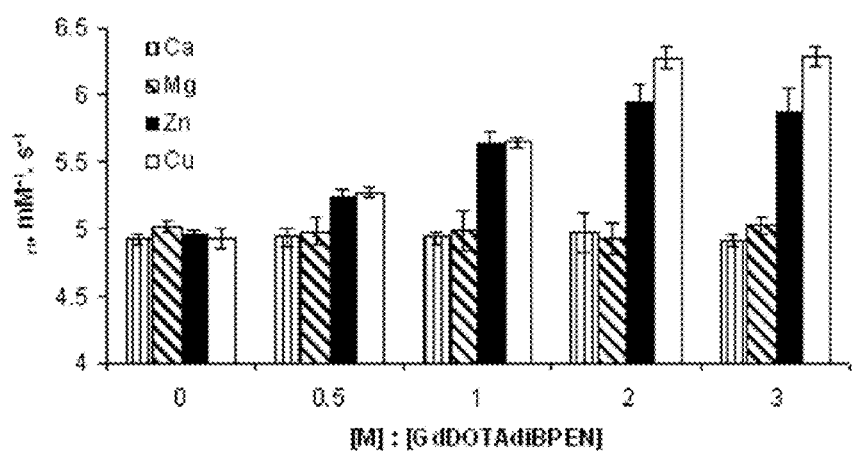
FIG. 7 shows a graph of the relaxivity of GdDOTA-diBPMA in 0.1 M Tris buffer pH 7.6 in presence and absence of different metal ions (M). Measurements done at 37° C., pH 7.6 0.1M Tris buffer, 23 MHz.

FIG. 5 shows an illustrative embodiment of a macrocycle-based agent for determining a zinc analyte. The compound includes two BPMA target binding units covalently attached to a tetraaza macrocycle the chelator. The synthesis of this agent is shown in FIG. 6b and follows the procedure described in some embodiments of the present invention. In absence of a metal the optical properties of the agent might be modified depending on the presence or absence of $Zn^{2+}$ the target. By addition of a paramagnetic metal (e.g. $Gd^{3+}$) an agent having an MRI signal can be generated. In the presence of zinc the BPMA units can bind to the target enhancing the relaxivity of the complex to generate a target-bound MRI signal. FIG. 7 shows an illustrative embodiment of the relaxivity properties of compound in FIG. 5 when the macrocycle chelates $Gd^{3+}$. The relaxivity increases with increasing amounts of zinc or copper but not with addition of calcium and magnesium, which indicates that the target binding units are selective for zinc and copper.

Figure 8:
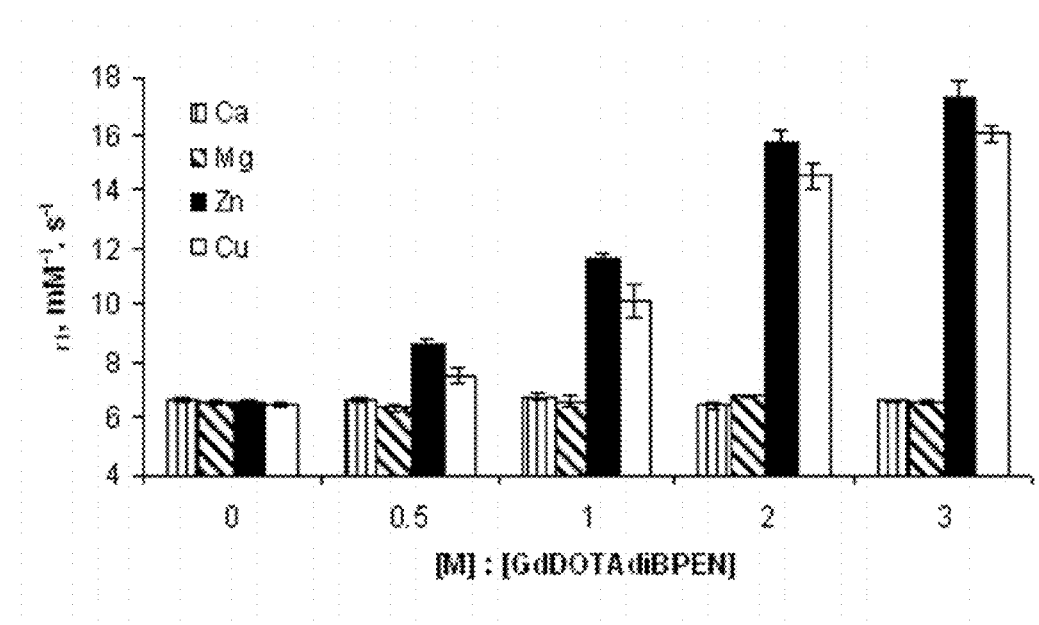
FIG. 8 shows a graph of the relaxivity of GdDOTA-diBPMA in 0.1 M Tris buffer pH 7.6 with human serum albumin 0.6 mM in presence and absence of different metal ions (M). Measurements done at 37° C., pH 7.6 0.1M Tris buffer, 23 MHz.
Figure 9:
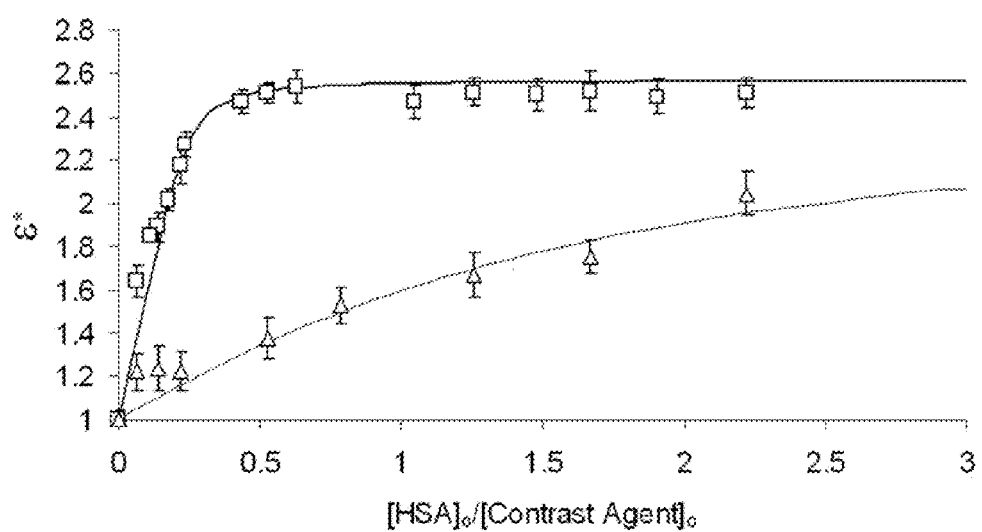
FIG. 9 shows a titration of GdDOTA-diBPEN 1 mM (triangles), and GdDOTA-diBPMA 1 mM plus 2 mM of $Zn^{2+}$ (squares) with HSA, the measured variable is an enhancement relaxation rate factor ($\epsilon^*$) which represents the ratio of the difference in relaxation rates of the contrast agent in buffer with HSA minus the relaxation rate of buffer HSA and the relaxation rate of the agent in buffer minus the relaxation rate of the buffer.
Figure 10:
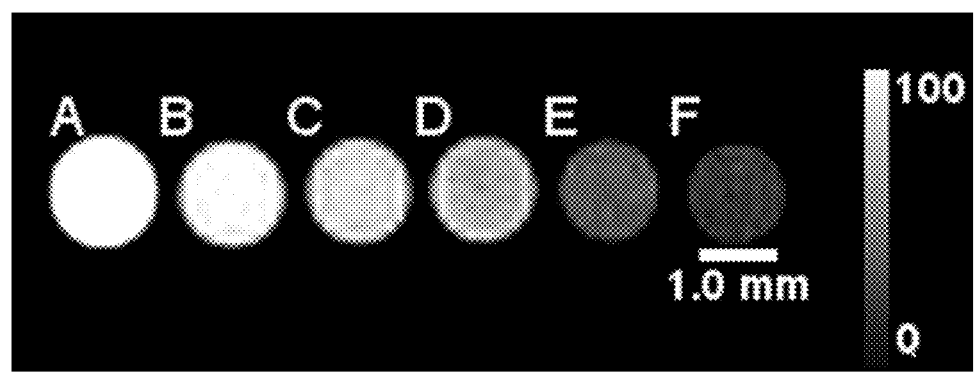
FIG. 10 shows a T1-weighted phantom MR images. Images of a 100 μM solution of GdDOTA-diBPMA in Tris buffer with 600 μM HSA at various concentrations of $ZnCl_2$. Spot A, 200 μM Zn; B, 100 μM Zn; C, 30 μM Zn; D, 0μM Zn; E, no contrast agent and F, Tris buffer without HSA and without contrast agent. Repetition time (TR)=200.0 ms; echo time (TE)=8.3 ms; data matrix=128×128. FOV=15×15 $mm^2$. Single scan, no averaging. A single slice of 5 mm was acquired centered at the sample height (10 mm)

In another embodiment the invention provides a method to enhance the longitudinal relaxivity of the agent upon binding to the target (e.g. $Zn^{2+}$) and subsequent binding to serum albumins such as human serum albumin (HSA) in humans as exemplified in FIGS. 8, 9 and 10.

In another embodiment the invention comprises MRI protocols in which the agent is deemed injected in low enough concentration as not to cause contrast enhancement in the absence of significant analyte, but exhibit contrast upon target release from cells, tissues or organs. In other embodiment, analogous PET/PET-CT and SPECT techniques with similar spatial-temporal-based applications of the analogs of the agents and or compositions described herein are also outlined using the appropriate radionuclides (e.g., $^{64}Cu$, or $^{86}Y$ for PET and $^{111}In$, or $^{99m}Tc$ for SPECT). Attachment of moieties such as dyes, nanoparticles, and quantum dots are also described for optical localization and imaging.

Figure 11:
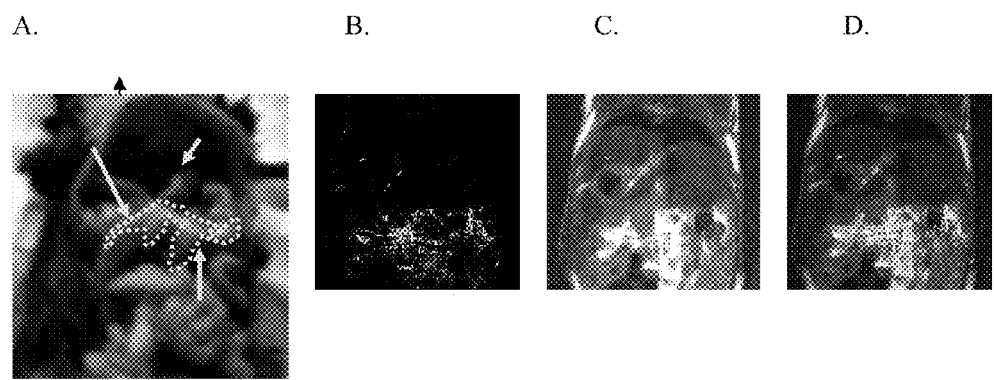
FIG. 11 shows in A) a post-mortem photograph of a mouse after midline laparotomy, the head of the mouse is in the top of the figure and the tail is in the bottom, the pancreas is delineated by the dotted line and positioned by the long arrow-head lines. The stomach and liver position is indicated by the small arrow-head line. In B) the difference MR Image of the corresponding alive glucose stimulated mouse before injection of $Gd^{3+}$ DOTAdiBPMA and after three minutes from the injection. The sites with enhancements due to zinc binding are shown as bright spots. In C) a proton-density with slight T1-weighted MR image slice of the pancreas of the corresponding mouse thoracic area is shown to highlight anatomical features. In D) the overlay of B and C is shown.
Figure 12:
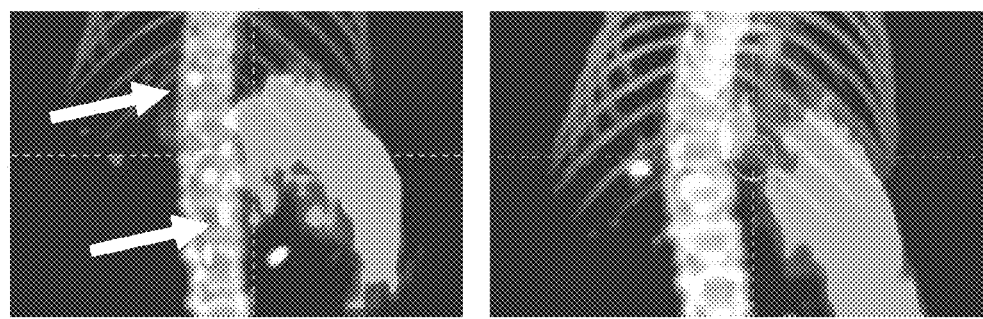
FIG. 12 shows PET images (overlayed on CT scans) of mice with high glucose (i.p injected with 20% glucose solution (2 g/kg body weight) (mouse 1, A) and low glucose (saline only) (mouse 2, B) after being injected with $^{64}Cu^{2+}$ DOTAdiBPMA. Note the absence of the pancreas islet signals in the low glucose compared to the high glucose mouse (white arrows).

In some embodiments of the invention the agent or compositions described herein allow to image localized sites of the target, e.g., $Zn^{2+}$ release in the pancreas upon glucose-stimulated insulin release (GSIS). Zinc, as free ions is released into the extracellular space of the beta cell in the pancreatic islets of Langerhans with insulin release. Such a release of insulin is, therefore, correlated with the release of $Zn^{2+}$ that is imaged with the contrast agent. Sample MRI and SPECT images of the animal trials are shown in FIGS. 11 and 12. This invention provides a way to image the event of insulin release in the functioning pancreas or pancreatic region.

Some embodiments of the present invention can advantageously provide agents or compositions that could image the accumulation of $Zn^{2+}$ in diseased states such as Alzheimer's disease in analogs that could cross the blood-brain barrier (e.g., with the right hydrophobicity index).

For example, an agent as described herein can provide a method of monitoring the levels of the target (e.g., $Zn^{2+}$) in the progression of a disease such as diabetes and Alzheimer's.

In some embodiments the invention provides a method of monitoring the levels of the target at extremely low administration concentration of the agent or composition such as in the micromolar range for MRI and nanomolar or lower with other nuclear imaging techniques that involving radionuclides (e.g., PET, SPECT).

In another embodiment the present invention can provide a process for the preparation of an agent of formula shown in FIGS. 1, 2, 3 and 4, said process including (i) an organic compound having binding affinity for an cell surface receptor to (ii) facilitate the retention of the contrast agent close to or near where the target metal ion is released or accumulating. The receptor must be detectable in an in vivo diagnostic imaging procedure; and the linker must couple vector to reporter, at least in significant degree until the imaging procedure has been completed.

In another embodiment the present invention can provide a process for the preparation of an agent formulation that will allow for the monitoring of the agent retention, retardation or accumulation with ultrasound. When the target (e.g., $Zn^{2+}$) binding domains are preserved and the ligand is connected to an ultrasound-visible entities such as microbubbles (or other particles with enhanced echogenicity), the invention allows for the localization of the sites that release or retain the target (e.g., $Zn^{2+}$).

In one embodiment, the agent can be a compound which does not elicit any unacceptable biological response, particularly compounds that act to sequester enzyme-bound or nucleic-acid bound metal ions and factors that cause blood-pressure modifying responses at the administration concentration. However, biological responses can, if desired, be modified by administration of a therapeutic agent, e.g., before, during or after administration of the agent of formula shown in FIGS. 1, 2, 3 and 4.

EXAMPLES $^{1}H$- and $^{13}C$-NMR spectra were recorded on a Varian Gemini: Unity plus 200 MHz. High resolution spectra were recorded on a Varian INOVA 400 MHz spectrometer. Data are reported in the following order: chemical shift in ppm (δ); muliplicities are indicated as b (broadened), s (singlet), d (doublet), t (triplet), q (quartet), m (multiplet); coupling constants, J, are reported in Hz; integration is provided. Mass spectra (MS) were measured either with a HPLC/ES-MS spectrometer Agilent 1100 Series LC/MSD trap or a Voyager-DE PRO Biospectrometry Workstation (MALDI-TOF)] operating in reflector mode using α-cyano-4-hydroxycinnamic acid as the matrix. HPLC purification was performed on a Hewlett Packard Series 1050 system using a Jupiter 10μ C18 300A 10 mm×250 mm column. MR images were obtained using a 400-MHz (9.4 T) vertical-bore Varian INOVA microimaging system. T1's were measured using a Maran Ultra NMR relaxometer operating at 23 MHz.

Relaxivity measurements. Longitudinal relaxivity values were determined from the slope of the line of the reciprocal of T1 versus the concentration of gadolinium. A 5 mM solution of the gadolinium complex was made up in Tris buffer 0.1 M pH 7.6 or in buffer plus HSA 600 μM or male human blood serum. These were serially diluted four times to give five different sample concentrations at a [Gd]:[Zn] ratio of 1:0. $ZnCl_2$ ($CuCl_2$) was added to each of the samples to give a [Gd]:[Zn] ratio of 1:0.5. After 30 min of incubation at 37° C., T1 measurements were made. This titration was repeated until a 1:3 ([Gd]:[Zn]) ratio was reached. Similar titration experiments were done with $CaCl_2$ and $MgCl_2$ to test the effects of competing cations.

MRI. In vitro phantom MR images were obtained of GdDOTA-diBPMA 0.1 mM in Tris buffer 0.1 M pH 7.6 plus HSA 600 µM, with 30, 100 and 200 µM $Zn^{2+}$ loaded in 1 mm capillary tubes. Images and T1 values were obtained on a 400-MHz (9.4 T) vertical-bore Varian NOVA microimaging system using a spin-echo multislice (SEMS) sequence. The following parameters were used: Repetition time (TR)=200.0 ms; echo time (TE)=8.3 ms; FOV 15×15 $mm^2$, data matrix=128×128. No average. A single slice of 5 mm was acquired centered at the sample height (10 mm). Image analyses were carried out using ImageJ 1.41o software provided by the National Institutes of Health, USA.

Determination of GdDOTA-$Zn_2$diBPMA-HSA dissociation constant by relaxometric demonstrations. HSA was titrated by adding increasing amounts of a GdDOTA-diBPMA 0.1 mM solution in Tris buffer 0.1 M pH 7.6 and the T1 values recorded.

Some embodiments of the present invention are also described in De Leon-Rodriguez et al. *J. AM CHEM. SOC.* 2009, 131, 11387-11391. The entire content is herein incorporated by reference in its entirety. More specifically, additional embodiments are incorporated by reference; none-limiting examples include modifications of the novel contrast agent, compound characterization, methods of use thereof, detailed preparation procedures, and in vivo and in vitro experimental results are incorporated herein in their entirety.

Example 1

1,4,7,10-tetraazacyclododecane-1,4-bis(N,N-bis(2-pyridylmethyl)aminoethyleneacetamide)-7,10-acetic acid, DOTA-diBPMA. To a solution of 1,4,7,10-Tetraazacyclododecane-1,4-bis(tert-butyl acetate)-7,10-acetic acid (166 mg, 0.321 mmol) in DMF (10 ml) was added a solution of HBTU (243 mg, 0.642 mmol) in DMF (5 mL). The mixture was stirred for 15 minutes at room temperature followed by slow addition of a solution of N,N-bis(2-pyridyl-methyl)ethylene diamine (BPMA) (155 mg, 0.642 mmol) in DMF. The mixture was stirred at room temperature overnight. The solvent was evaporated and the residue was taken into $CHCl_3$ (20 mL) and washed with deionized water (1×10 mL) and then extracted to the aqueous phase with acetic acid 1M (3×20 mL). The collected aqueous phases were then basified to pH 13 and the product extracted with $CHCl_3$ (3×20 mL). The combined organic phases were dried with anhydrous $K_2CO_3$ and the solvent was removed by rotary evaporation yielding an orange oil (230 mg, 74%). $^1$H NMR (200 MHz, $CDCl_3$; TMS): δ 1.32 (18 H, s, tbut), 2.2-3.2 (32H, bm, —$CH_2$—), 3.84 (8H, s, N—$CH_2$-py), 7.15 (4H, t, 5-H, $^3J_{HH}$=6.4), 7.31 (4H, d, 3-H, $^2J_{HH}$=7.7), 7.63 (4H, t, 4-H, $^3J_{HH}$=7.6), 8.52 (4H, d, 6-H, $^2J_{HH}$=4.6). $^{13}$C NMR (200 MHz, $CDCl_3$, TMS): δ 28.2, 50.2, 53.0, 55.8, 56.6, 60.1, 77.4, 81.6, 122.4, 123.45, 136.9, 149.1, 159.3, 171.1, 171.8. MS (ESI-positive) m/z=966 [M+H]+ (calcld 966).

A solution of the previous compound (60 mg) in $CH_2Cl_2$, was added drop wise a solution of trifluoroacetic acid (1.5 mL) in $CH_2Cl_2$ (2 mL). The resultant solution was stirred for 2 hours and then the solvent was removed by rotary evaporation. The residue was washed with cold ethyl ether (3×10 mL) and then was taken into deionized water with HCl 0.1 M (10 mL) and washed with $CHCl_3$ (3×10 mL). The aqueous phase was freeze dried yielding a highly hygroscopic orange solid (quant.). $^1$H NMR (200 MHz, $D_2O$): δ 2.6-3.5 (28H, bm, —$CH_2$—), 3.67 (4H, s, —$CH_2$—), 3.85 (8H, s, N—$CH_2$-py), 7.25 (4H, t, 5-H, $^3J_{HH}$=6.8), 7.38 (4H, d, 3-H, $^2J_H$H=7.9), 7.73 (4H, t, 4-H, $^3J_{HH}$=7.5), 8.33 (4H, d, 6-H, $^2J_{HH}$=4.9). $^{13}$C{$^1$H}NMR (50 MHz, $D_2O$): δ6.8, 48.0, 51.1, 53.0, 55.3, 56.3, 59.2, 123.1, 124.4, 138.1, 147.7, 156.7, 169.0, 171.7. MS (ESI-positive) m/z=826 [M+H]+ (calcld 826).

General procedure for $Gd^{3+}$ and other metal ions DOTA-diBPMA synthesis. DOTA-diBPMA was dissolved in MilliQ grade $H_2O$ and the pH adjusted to 6.5 with 1 M NaOH. $GdCl_3.6H_2O$ in slight excess was slowly added. The pH of the solution was maintained between 6 and 6.5 during addition. Resultant solution was stirred at room temperature for several days and pH adjusted close to 6.5 as needed. Unreacted $Gd^{3+}$ was precipitated as $Gd(OH)_3$ after the addition of 1 M NaOH and the crude mixture was purified by semi-preparative HPLC with aqueous $(NH_4)_2CO_3$ 5 mM pH 8/MeOH (50/50) as the eluant. The complex was obtained as a yellow solid. m/z (MALDI+) m/z=1008.67 [M+H]+ (calcld. 1008.26). Anal. Calcd for $C_{44}H_{58}GdN_{12}O_6.2H_2O$: C, 50.61; H, 5.98; N, 16.10. Found: C, 50.81; H, 5.96; N, 16.18.

Example 2

The following example describes the use of GdDOTA-diBPMA in the in vivo imaging of $Zn^{2+}$ by MRI. GdDOTA-diBPMA was shown to bind to $Zn^{2+}$ tightly and as such bind to serum albumin. For this study, rodents (rats and mice) were fasted overnight (12-16 hours) before treatment. Thereafter, an intraperitoneal (i.p.) injection of 20% glucose solution was given, then a solution of GdDOTA-diBPMA was injected intravenously (e.g., tail vein) within a 20 minute window as a bolus. The dynamic contrast enhancement (DCE) was monitored prior to until after 30 min to 2 hrs of the i.p. injection of glucose and the administration of the contrast agent. The T1-based contrast enhancement that was observed only in animals injected with glucose versus normal saline solution as control showed the sites (e.g., in the pancreas) that release $Zn^{2+}$ ions (FIG. 11).

Example 3

The following example describes the use of GdDOTA-diBPMA in the in vivo imaging of $Zn^{2+}$ by MRI as applied to delineate diabetic versus normal physiology. In this example, the presence or absence of the contrast enhancement is directly correlated with the presence or absence of insulin-releasing sites in the pancreas or zinc containing, retaining or releasing sites in other parts of the body. The same fasting method and imaging was done for animals as in Example 2 above. The animals were induced to be type I diabetic by treatment with the antibiotic streptozotocin for 5 days and imaged by MRI after testing to by symptomatic of diabetes. The MR imaging protocol used for these animals were the same as the ones used on them prior to being diabetes (e.g., glucose by i.p. injection and compound 1 treatment prior to T1-weighted DCE). The differences in contrast enhancement, e.g., the general lowering and/or disappearance of T1-weighted contrast enhancement from the normal to diabetic state, was observed both for individual animals and as a general trend. The disappearance of localized and MRI-observable T1-enhancements (as observed in FIG. 11B) in the pancreas was correlated with the disappearance of functioning beta-cell containing islets of Langerhans in the pancreas. The beta cells, which release the insulin, are know to corelease zinc ions into the extracellular space at the same time upon glucose-stimulated insulin secretion.

Example 4

The following example describes the use of compound $^{64}Cu^{2+}$ DOTA-diBPMA (analog of GdDOTA-diBPMA) in the in vivo imaging of $Zn^{2+}$ by PET. The same overnight fasting treatment and imaging of the animals prior to GSIS and intravenous contrast agent administration was done as in Example 2. The PET imaging of the animals, both pre- and post-diabetic states, was done prior to, during and after contrast agent injection. It was observed that the fasted animals that were not treated or stimulated with glucose did not show pronounced contrast enhancement, unlike in the glucose-stimulated animal group which showed numerous sites in the pancreas that showed signal enhancement with PET. It was also observed that the animals lost significant localized pancreas enhancement after streptozotocin treatment (i.e., diabetic state) when given the same PET imaging treatment protocol (FIG. 12).

Example 5

The following example describes the use of GdDOTA-diBPMA for MRI or its PET analog ($^{64}Cu^{2+}$ DOTA-diBPMA) for mapping the Zn-binding capacity of an animal. Low blood levels of the GdDOTA-diBPMA (sub-millimolar) or its PET analog ($^{64}Cu^{2+}$ DOTA-diBPMA; at nanomolar or sub-nanomolar levels) can be injected directly into the bloodstream to map the parts of the body that can have enough of the metal ion that can be chelated and bound to serum albumin and followed by dynamic scanning by MRI and PET, respectively. The T1-enhancement that develops during the blood lifetime of the agent(s) allows for the imaging of normal or diseased tissues that can retain, retard or accumulate the agent-bound zinc by MRI. Also, the PET-analog can give a map of cells, tissues or organs that release or have available $Zn^{2+}$ ions by PET imaging with or without chemical (e.g., glucose or other substrates) stimulation. Such diseased states include, but are not limited to prostate and other types of cancer, Alzheimer's disease, and diabetes.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification can mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:
1. A MRI, PET, CT, X-ray, SPECT, optical or ultrasound agent or composition having formula:

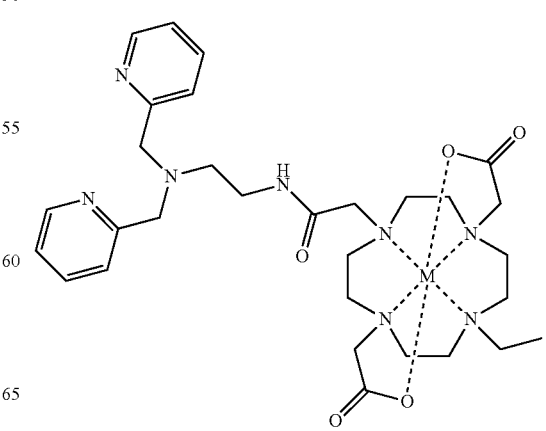

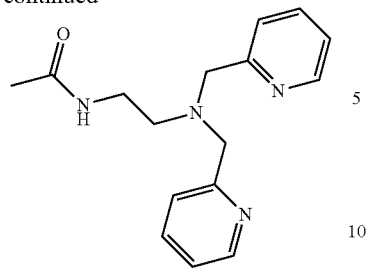

wherein M is a metal selected from the group consisting of $Gd^{3+}$, $Eu^{3+}$, $Tm^{3+}$, $Dy^{3+}$, $Tb^{3+}$, $Yb^{3+}$, $Mn^{2+}$, $^{111}In^{3+}$, $^{113m}In^{3+}$, $^{67}Ga^{3+}$, $^{68}Ga^{3+}$, $^{99m}Tc^{4+}$, $^{64}Cu^{2+}$, $Tl^{3+}$, $^{153}Sm^{3+}$, $^{166}Ho^{3+}$, $^{212}Bi^{3+}$, $^{90}Y^{3+}$, $^{377}Lu^{3+}$, $^{225}Ac^{3+}$, $^{149}Pm$, $^{159}Gd$, $^{140}La$, $^{175}Yb$, $^{47}Sc$, $^{186}Re$, $^{97}Ru$, $^{105}Rh$, $^{109}Pd$, $^{197}Pt$, $^{67}Cu$, $^{198}Au$, $^{117m}Sn$, $^{212}Pb$, Ce, Pr, Nd, Pm, Sm, Ho, Er, Lu, and Y; and wherein the agent or composition is capable of detecting a target in vivo in a subject.

2. The agent or composition according to claim 1, wherein the target is a metal ion or a macromolecular receptor.

3. The agent or composition according to claim 1, wherein the target is $Zn^{2+}$ or $Cu^{2+}$.

* * * * *